US010023515B2

(12) United States Patent
Li et al.

(10) Patent No.: US 10,023,515 B2
(45) Date of Patent: Jul. 17, 2018

(54) METHOD FOR PREPARING CYCLOHEXANONE BY HYDROGENATING PHENOL

(71) Applicant: China Petrochemical Development Corporation, Taipei (TW)

(72) Inventors: Chien-Hsien Li, Taipei (TW); Hung-Lung Chen, Taipei (TW); Ming-Syun Yang, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 15/591,296

(22) Filed: May 10, 2017

(65) Prior Publication Data

US 2018/0072646 A1 Mar. 15, 2018

(30) Foreign Application Priority Data

Sep. 9, 2016 (TW) ............................ 105129292 A

(51) Int. Cl.

*C07C 45/00* (2006.01)
*B01J 19/00* (2006.01)
*B01J 19/24* (2006.01)

(52) U.S. Cl.

CPC ............. *C07C 45/006* (2013.01); *B01J 19/24* (2013.01); *B01J 2219/24* (2013.01)

(58) Field of Classification Search

CPC ............................... C07C 45/006; B01J 19/24
USPC ......................................................... 568/362
See application file for complete search history.

(56) References Cited

U.S. PATENT DOCUMENTS 3,998,884 A * 12/1976 Gibson ................. C07C 45/006 568/362
4,410,741 A * 10/1983 Van Peppen ............ C07C 29/20 568/835

FOREIGN PATENT DOCUMENTS

| | | | |
|---|---|---|---|
| CN | 105073700 | A | 11/2015 |
| GB | 890095 | A | 2/1962 |
| TW | 201235343 | A | 9/2012 |
| TW | I522341 | B | 2/2016 |
| WO | 2009080618 | A1 | 7/2009 |
| WO | 2009080620 | A1 | 7/2009 |
| WO | 2009131769 | A1 | 10/2009 |

OTHER PUBLICATIONS

Taiwanese Office Action dated Oct. 26, 2017 in corresponding Taiwan Patent Application No. 10621091780.

* cited by examiner

*Primary Examiner* — Sikarl A Witherspoon
(74) *Attorney, Agent, or Firm* — Mintz Levin Cohn Ferris Glovsky and Popeo, P.C.; Peter F. Corless

(57) ABSTRACT

A method of preparing cyclohexanone by hydrogenating phenol is provided. The method includes a step of introducing an additional flammable gas to dilute hydrogen gas concentration, so as to increase the throughput and decrease energy consumption. Further, the discharged residual gases from the hydrogenation of phenol have a calorific value. Also provided is a system for generating cyclohexanone by hydrogenating phenol.

16 Claims, 2 Drawing Sheets

METHOD FOR PREPARING CYCLOHEXANONE BY HYDROGENATING PHENOL

CROSS-REFERENCE TO RELATED APPLICATION

This application claims under 35 U.S.C. § 119(a) the benefit of Taiwanese Patent Application No. 105129292 filed Sep. 9, 2016, the entire contents of which are incorporated herein by reference.

BACKGROUND

1. Technical Field

The present disclosure relates to hydrogenation of phenol, and more particularly, to a method for generating cyclohexanone by adjusting the hydrogen gas concentration for hydrogenation of phenol by using a flammable gas for dilution.

2. Description of Related Art

Cyclohexanone is an important intermediate during the production of caprolactam, which is an important monomer to form nylon-6. In the industry, cyclohexanone is mainly generated by hydrogenating cyclohexane or phenol. Stringent reaction conditions for hydrogenating cyclohexane are needed. Byproducts, such as cyclohexanol and organic acids, are generated during the reaction, leading to a low conversion rate of and a low selectivity for cyclohexanone. In the industry, there exist issues of high energy consumption and separation complexity in the preparation of cyclohexanone.

There are two ways to produce cyclohexanone by hydrogenating phenol, i.e., a one-step method in which phenol is used as a starting material to directly generate cyclohexanone, and a two-step method in which cyclohexanol is generated as an intermediate, from which a final cyclohexanone product is generated. In the two-step method, dehydrogenation of cyclohexanol requires an excessive amount of thermal energy. In the comparison of the two methods, the one-step method has obvious advantages in that it is less energy-consuming and cost-effective than the two-step method. Further, the one-step method can be conducted either in a liquid or solid state.

During the preparation of phenol directly to cyclohexanone in the one-step method, there are various byproducts generated, such as cyclohexanol and others. Many purifying steps and methods are thus involved. For example, patent publication, such as WO 2009/131769A1, WO 2009/080618A1, and WO 2009/080620A1, disclose that multiple distillation processes and purifying steps involving the hydrogenation of phenol to prepare cyclohexanone are involved. Further, U.S. Pat. No. 4,410,741 discloses a batch-type preparation using a nickel catalyst mixed with liquid phenol at controlled temperature, pressure, and ratio of hydrogen gas to nitrogen gas in a reactor to generate cyclohexanone.

However, in the citations above, in order to overcome the defect of poor selectivity in the reaction, multiple distilling and purifying steps are added at the end of reaction, or the catalytic activity has to be improved to raise the product selectivity.

In addition, referring to TWI522341, additional nitrogen gas is introduced to raise the throughput, the end gases in this process contain 30 mole % to 80 mole % of inflammable nitrogen gas. Thus, this leads to the low calorific value of the end gases, making them difficult for further use.

In view of the problems above, there still exists a need to develop a highly efficient method with economic values to resolve the above inherent issues associated with the generation of cyclohexanone by hydrogenating phenol in commercial applications.

SUMMARY

The present disclosure provides a method including a step of introducing an additional flammable gas to dilute a hydrogen gas concentration for generating cyclohexanone by hydrogenating phenol that can increase throughput and reduce energy consumption, and can also bring about a higher caloric value due to the flammable gas mainly found among the residual gases.

The present disclosure provides a method for preparing cyclohexanone, comprising a step of hydrogenating phenol in the presence of hydrogen gas, a flammable gas for dilution, and a catalyst comprising at least one Group 10 metal.

In addition to providing fresh hydrogen gas and flammable gas for dilution in the preparation method of the present disclosure, the required hydrogen gas concentration for hydrogenation can be obtained by using a compressor to adjust the hydrogen gas concentration with the residual gases after hydrogenation in the reactor.

The present disclosure further provides a system for generating cyclohexanone by hydrogenating phenol, comprising:

a reactor configured to generate cyclohexanone and residual gases by hydrogenating phenol with hydrogen gas, wherein the reactor comprises a flammable gas for dilution;

a separator connected to the reactor and configured to receive and separate cyclohexanone from the residual gases generated in the reactor;

a compressor connected to the separator and the reactor and configured to recycle at least a part of the residual gases separated from the separator back to the reactor to adjust the hydrogen gas concentration therein; and a burning furnace connected to the separator and configured to burn a part of the residual gases separated from the separator to generate thermal energy.

The method provided by the present disclosure uses a flammable gas to adjust the required hydrogen gas concentration in a method for preparing cyclohexanone by hydrogenating gaseous phenol without affecting the proceeding of the reaction, while maintaining a high conversion rate and raising the selectivity for the cyclohexanone product. During the process, the residual gases mainly include the flammable gas and have a higher calorific value. Thus, the residual gases can be further used as an auxiliary fuel for the preparation. Furthermore, the method of the present disclosure can be adapted to different properties of the catalyst.

DETAILED DESCRIPTION OF EMBODIMENTS

Figure 1:
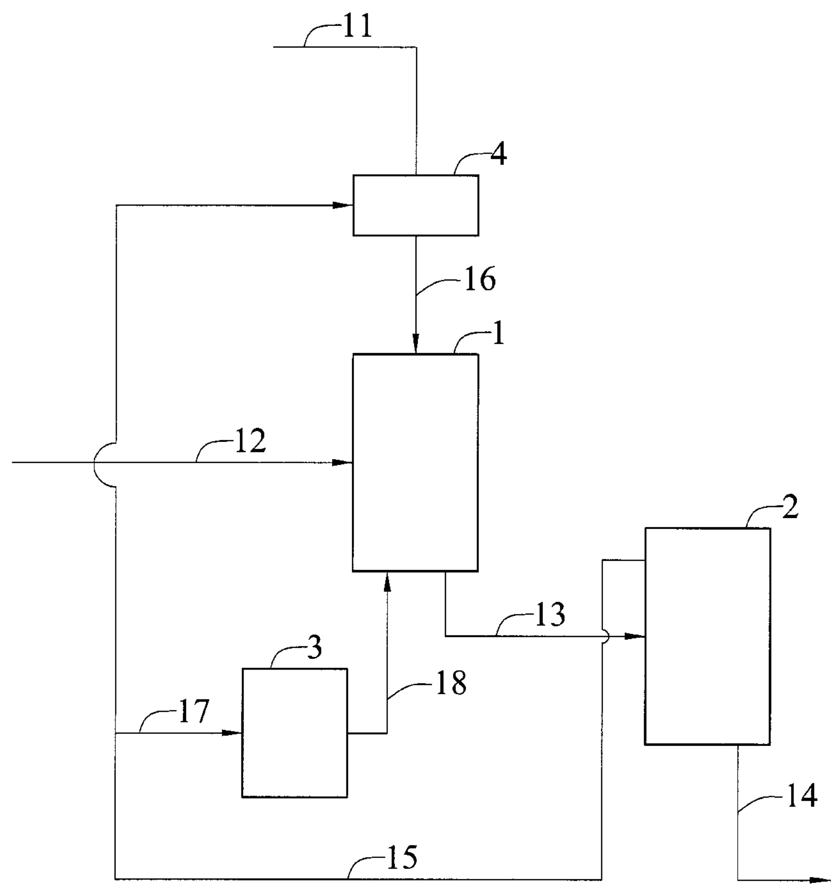
FIG. 1 is a schematic diagram of a system for generating cyclohexanone by hydrogenating phenol of the present disclosure.

The following examples are used to illustrate the present disclosure. However, these examples are only illustrative of the present disclosure, and in no way limiting the claims of the present disclosure. The present disclosure can be implemented or applied based on other different embodiments. Each of the details in the present specification can be modified and altered based on different views and applications, without departing from the spirit of the disclosure of the present disclosure.

The present disclosure provides a method for preparing cyclohexanone, comprising the step of: hydrogenating phenol in the presence of hydrogen gas, a flammable gas for dilution, and a catalyst comprising at least one Group 10 metal.

In one embodiment, while the hydrogenation proceeds, the hydrogen gas concentration ranges from 30 mole % to 80 mole %, based on the total amount of gases.

In addition to providing fresh hydrogen gas and flammable gas for dilution in the preparation method of the present disclosure, the required hydrogen gas concentration for hydrogenation can be obtained by using a compressor to adjust the hydrogen gas concentration with the residual gases after hydrogenation in the reactor.

According to one preferred embodiment of the present disclosure, a catalyst comprising at least one Group 10 metal is filled in a reactor, wherein the catalyst has a catalytic activity for hydrogenation at temperature of 150 to 200° C. and under a pressure of 0 to 22 psig (pound per square inch on a scale) to convert phenol into cyclohexanone. During the early stage of the reaction, reactant phenol is made molten by heating a feeding slot and then being delivered by a metering pump, the reactant phenol is vaporized in advance at a preheating section, and then the flammable gas for dilution and hydrogen gas are introduced into the reactor. The presence of the catalyst filled in the interior of the reactor catalyzes the hydrogenation of phenol. The products generated are sampled and collected after going through the separator. At least a part of the residual gases is recycled back to the reactor by a compressor to adjust the hydrogen gas concentration in hydrogenation.

In light of the above descriptions, the system of generating cyclohexanone by hydrogenating phenol of the present disclosure comprises:

a reactor configured to generate cyclohexanone and residual gases by hydrogenating phenol with hydrogen gas, wherein the reactor comprises a flammable gas for dilution;

a separator connected to the reactor and configured to receive and separate cyclohexanone from the residual gases generated in the reactor;

a compressor connected to the separator and the reactor and configured to recycle at least a part of the residual gases separated from the separator back to the reactor to adjust the hydrogen gas concentration therein; and a burning furnace, directly or indirectly connected to the separator, and configured to burn a part of the residual gases separated from the separator to generate thermal energy.

In one embodiment, the burning furnace is connected to the separator via a buffer tank.

In one embodiment, when the hydrogenation takes place in the reactor, the hydrogen gas concentration ranges from 30 mole % to 80 mole %, based on the total amount of gases.

In one embodiment, the separator separates the residual gases from the generated cyclohexanone gas by using different boiling points. Then, cyclohexanone gas is condensed to a liquid form, and the gas and the liquid are subsequently separated based on the different densities of gas and liquid.

In one embodiment, the burning furnace uses the thermal energy to heat water to generate steam as a heat source for the reactor.

In another embodiment, the burning furnace is connected to the reactor via pipelines to provide steam to the reactor.

FIG. 1 is an embodiment of a system for generating cyclohexanone by hydrogenating phenol of the present disclosure, wherein the system comprises a reactor 1, a separator 2, a burning furnace 3, a compressor 4, and pipelines 11-18.

In one embodiment of the present disclosure, initial gases (i.e., the flammable gas for dilution and hydrogen gas) and gaseous phenol are fed into the reactor 1 via the pipelines 11 and 12, respectively, to start a reaction. The cyclohexanone product and the residual gases are introduced into the separator 2 via the pipeline 13. Then, the obtained cyclohexanone product is fed out via the pipeline 14, and the residual gases are fed into the compressor 4 via the pipeline 15 to adjust the hydrogen gas concentration entering the reactor 1. Afterwards, the adjusted gas is fed into the reactor 1 via the pipeline 16. Furthermore, a part of the residual gases is delivered to the burning furnace 3 for use as an auxiliary fuel via the pipeline 17, which is connected to the pipeline 15. The thermal energy generated in the burning furnace 3 is supplied to the reactor 1 for use via the pipeline 18.

In one embodiment, the thermal energy is used to heat water to generate steam as a heat source for the reactor.

In one embodiment of the present disclosure, the initial gas (in the pipeline 11) comprises a flammable gas for dilution and hydrogen gas, wherein the molar concentration of hydrogen gas is 99.9 mole %. The molar concentration of hydrogen gas ranges from 10 mole % to 35 mole %, based on the total amount of the residual gases after hydrogenation (in the pipelines 13 and 15). After adjustment, the gas (in the pipeline 16) is fed into the reactor, wherein the hydrogen gas concentration in the reactor ranges from 30 mole % to 80 mole %.

In the preparation method of the present disclosure, other gases (such as nitrogen gas) can be introduced into the reactor to adjust the hydrogen gas concentration required for the hydrogenation reaction.

Figure 2:
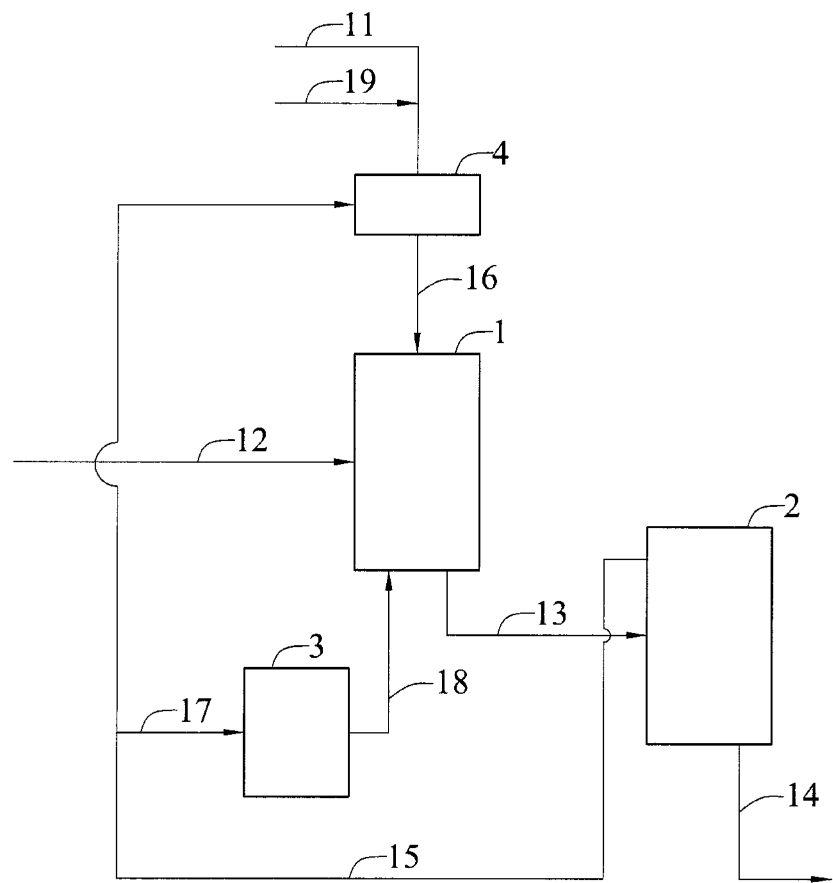
FIG. 2 is another schematic diagram of a system for generating cyclohexanone by hydrogenating phenol of the present disclosure.

FIG. 2 is an embodiment of a system for generating cyclohexanone by hydrogenating phenol of the present disclosure. The system comprises the reactor 1, the separator 2, the burning furnace 3, the compressor 4, and the pipelines 11 to 18 and a pipeline 19.

In another embodiment of the present disclosure, the initial gases and nitrogen gas are fed into the reactor via the pipeline 11 and 19, respectively, and gaseous phenol is fed into the reactor via the pipeline 12 to proceed the reaction. The cyclohexanone product and the residual gases after the reaction are fed into a separator 2 via the pipeline 13. The obtained cyclohexanone product is fed out via the pipeline 14, and the residual gases are delivered into a compressor 4 via the pipeline 15 to adjust the hydrogen gas concentration before entering into the reactor 1. The adjusted gases are fed into the reactor 1 via the pipeline 16. In addition, a part of the residual gases are fed into the burning furnace 3 via the pipeline 17 to be used as an auxiliary fuel. The thermal energy generated in the burning furnace 3 is supplied to the reactor 1 for use via the pipeline 18. For example, the thermal energy is used to heat water to generate steam as a heat source for the reactor 1.

In the preparation method of the present disclosure, when hydrogenation proceeds, the hydrogen gas concentration ranges from 30 mole % to 80 mole %, based on the total amount of gases, wherein the catalyst comprises 0.5 wt % to 1.0 wt % of a Group 10 metal, for example, a Group 10 metal selected from platinum and palladium (preferable palladium), and hydrogenation takes places at molar ratio of hydrogen gas to phenol of 3 to 8.

Further, the flammable gas for dilution is one or more selected from C1 to C5 alkanes, and the examples of the C1 to C5 alkanes include methane, ethane, propane, butane, and pentane. In one embodiment, the flammable gas for dilution includes methane. For example, the flammable gas for dilution is natural gas. Although natural gas may contain carbon dioxide, the proceeding of the reaction is not affected.

Examples 1 to 3: Preparation of Cyclohexanone Using a Flammable Gas for Dilution In the preparation of cyclohexanone, the initial gases include 99.9 mole % of hydrogen gas and 0.01 mole % of natural gas. The gases generated after reaction are fed into the reactor via a recycling pipeline. After adjustment, the quantities of hydrogen gas and natural gas are listed in Table 1.

The reactor conditions: a weight hourly space velocity (WHSV) of 1.5 to 2.3, a molar ratio of hydrogen gas to phenol of 3 to 8, a reaction pressure of 22 psig, and a Johnson Matthey commercial catalyst (Type 355, containing 0.8% palladium) were used.

Equation for calculating a calorific value=(molar concentration of hydrogen gas in reactor (%)× calorific value of hydrogen gas)+(molar concentration of gases (natural gas/nitrogen gas) for dilution in reactor (%)×calorific value of gases for dilution (natural gas/nitrogen gas)

(Note: the calorific value of hydrogen gas was 2900 Kcal/$M^3$, the calorific value of the natural gas was 9750 Kcal/$M^3$, and the calorific value of nitrogen gas was 0 Kcal/$M^3$.)

The product and the generated gases after the reaction were fed into the separator to obtain cyclohexanone. In addition, a part of the residual gases (end gases) was fed into the burning furnace for use as an auxiliary fuel, wherein the calorific values of the end gases are listed in Table 1.

Comparative Example 1 Preparation of Cyclohexanone without Using a Flammable Gas for Dilution The process was the same as those in the other examples, except that the natural gas in the examples as replaced with nitrogen gas.

TABLE 1

| | Molar concentration of hydrogen gas in reactor | Molar concentration of gas for dilution (natural gas) in reactor | Molar concentration of gas for dilution in reactor | Conversion rate (%) | Selectivity for cyclohexanone (%) | Calorific value of residual gases (Kcal/$M^3$) |
|---|---|---|---|---|---|---|
| Example 1 | 41.97 | 56.39 | 0.0 | 99.39 | 93.20 | 6715 |
| Example 2 | 52.48 | 43.53 | 0.0 | 99.26 | 92.10 | 5766 |
| Example 3 | 59.23 | 38.83 | 0.0 | 99.15 | 92.24 | 5504 |
| Comparative example 1 | 53.99 | 0.0 | 45.95 | 99.06 | 92.22 | 1566 |

What is claimed is:

1. A method for preparing cyclohexanone, comprising hydrogenating phenol in the presence of hydrogen gas, a flammable gas for dilution and a catalyst comprising at least one Group 10 metal, wherein the flammable gas is a nature gas.

2. The method according to claim 1, wherein the hydrogen gas is at a concentration of from 30 mole % to 80 mole %, based on a total amount of gases, during the hydrogenating.

3. The method according to claim 1, wherein the hydrogenation of phenol is performed under a pressure of from 0 psig to 22 psig.

4. The method according to claim 1, wherein the hydrogenation of phenol is performed at a temperature of from 150° C. to 200° C.

5. The method according to claim 1, wherein the hydrogenation of phenol is performed at a molar ratio of the hydrogen gas to the phenol of from 3 to 8.

6. The method according to claim 1, wherein the Group 10 metal is palladium.

7. The method according to claim 1, wherein the catalyst comprises 0.5 wt % to 1.0 wt % of the Group 10 metal.

8. A system, comprising:

a reactor configured to generate cyclohexanone and residual gases by hydrogenating phenol with hydrogen gas, wherein the reactor comprises a flammable gas for dilution;

a separator connected to the reactor and configured to receive and separate the cyclohexanone from the residual gases generated in the reactor;

a compressor connected to the separator and the reactor and configured to recycle at least a part of the residual gases separated from the separator back to the reactor to adjust a concentration of the hydrogen gas in the reactor; and a burning furnace connected to the separator and configured to burn a part of the residual gases separated from the separator to generate thermal energy.

9. The system according to claim 8, wherein the hydrogen gas is at a concentration in a range of from 30 mole % to 80 mole %, based on a total amount of gases, during the hydrogenating.

10. The system according to claim 8, wherein the burning furnace generates steam as a heat source for the reactor by using the thermal energy to heat water.

11. The system according to claim 8, wherein the flammable gas comprises one or more gases selected from the group consisting of C1 to C5 alkanes.

12. The system according to claim 8, wherein the flammable gas comprises methane.

13. The system according to claim 8, wherein the flammable gas is a natural gas.

14. The system according to claim 8, further comprising filling the reactor with a catalyst comprising a Group 10 metal.

15. The system according to claim 14, wherein the Group 10 metal is palladium.

16. The system according to claim 14, wherein the catalyst comprises 0.5 wt % to 1.0 wt % of the Group 10 metal.

* * * * *